US011129546B1

(12) United States Patent
Dietrich et al.

(10) Patent No.: US 11,129,546 B1
(45) Date of Patent: Sep. 28, 2021

(54) PORTABLE UNIT FOR METABOLIC ANALYSIS

(71) Applicant: United States of Americas as represented by the Administrator of NASA, Washingon, DC (US)

(72) Inventors: Daniel L. Dietrich, Westlake, OH (US); Jeffrey R. Juergens, Parma Heights, OH (US); Mark E. Lewis, Merritt Island, FL (US); Nancy C. Piltch, Olmsted Falls, OH (US); Michael J. Lichter, Strongsville, OH (US); Russel W. Valentine, Wadsworth, OH (US); Dale M. Diedrick, Elyria, OH (US); Richard D Pettegrew, Parma Heights, OH (US); Peter M. Struk, Olmsted Township, OH (US)

(73) Assignee: United States of America as Represented by the Administrator of National Aeronautics and Space Administration, Washington, DC (US)

( * ) Notice: Subject to any disclaimer, the term of this patent is extended or adjusted under 35 U.S.C. 154(b) by 485 days.

(21) Appl. No.: 16/056,153

(22) Filed: Aug. 6, 2018

Related U.S. Application Data

(63) Continuation of application No. 11/677,654, filed on Feb. 22, 2007, now Pat. No. 10,076,268.

(51) Int. Cl.
*A61B 5/083* (2006.01)
*A61B 5/087* (2006.01)
(Continued)

(52) U.S. Cl.
CPC .............. *A61B 5/083* (2013.01); *A61B 5/082* (2013.01); *A61B 5/087* (2013.01); *A61B 5/0836* (2013.01);
(Continued)

(58) Field of Classification Search
CPC ....... A61B 5/097; A61B 5/082; A61B 5/4836; A61B 5/083; A61B 5/0836; A61B 2010/0087; A61B 5/08
See application file for complete search history.

(56) References Cited

U.S. PATENT DOCUMENTS 4,658,832 A  4/1987  Brugnoli
5,038,773 A  8/1991  Norlien et al.
(Continued)

OTHER PUBLICATIONS

Jaeger-Toennies, Oxycon Mobile, manufacturer's brochure from VIASYS Healthcare Inc., located at 22745 Savi Ranch Parkway in Yorba Linda, CA 92887-4668.

*Primary Examiner* — Christian Jang
*Assistant Examiner* — Karen E Toth
(74) *Attorney, Agent, or Firm* — Robert H. Earp, III; Mark Wolfgang; Helen M. Galus

(57) ABSTRACT

A portable unit for metabolic analysis includes a manifold in fluid communication with a mouth of a test subject. A conduit extends from the manifold and defines a flow channel through which the breaths of the test subject travels. A carbon dioxide sensor is attached to the conduit. The carbon dioxide sensor includes an intermediate support housing enclosing a volume disposed along the flow channel to define a first part of the flow channel, an inner support housing attached to a first side of the intermediate support housing, a plurality of IR LEDs mounted to an interior surface of the inner support housing, an outer support housing attached to a second side of the intermediate support housing, and a photodetector attached to the outer support housing. The photodetector faces the flow channel and receives IR radiation emitted by the plurality of LEDs.

19 Claims, 7 Drawing Sheets

(51) Int. Cl.
    *A61B 5/08*       (2006.01)
    *A61B 5/00*       (2006.01)
    *A61B 5/097*     (2006.01)
    *G01N 33/497*   (2006.01)
    *A61B 10/00*     (2006.01)

(52) U.S. Cl.
    CPC ............ *A61B 5/097* (2013.01); *A61B 5/4836* (2013.01); *A61B 5/08* (2013.01); *A61B 2010/0087* (2013.01); *G01N 33/497* (2013.01)

(56) References Cited

U.S. PATENT DOCUMENTS

| | | | |
|---|---|---|---|
| 5,119,825 A | | 6/1992 | Huhn |
| 5,261,415 A | * | 11/1993 | Dussault .............. A61B 5/0836 250/339.13 |
| 6,534,769 B1 | * | 3/2003 | Graham ............... A61B 5/0836 250/343 |
| 6,554,776 B1 | | 4/2003 | Snow et al. |
| 6,581,595 B1 | | 6/2003 | Murdock et al. |
| 2005/0145796 A1 | * | 7/2005 | Davis ..................... A61B 5/083 250/343 |
| 2007/0068811 A1 | * | 3/2007 | Tsukashima ......... G01N 33/497 204/433 |

\* cited by examiner

PORTABLE UNIT FOR METABOLIC ANALYSIS

CROSS-REFERENCE TO RELATED APPLICATION

This application is continuation of, and claims priority to, U.S. patent application Ser. No. 11/677,654 entitled "Portable Unit for Metabolic Analysis," filed on Feb. 22, 2007. The subject matter of this earlier-filed application is hereby incorporated by reference in its entirety.

ORIGIN OF INVENTION

The present disclosure is based on work performed by employees of the United States Government and may be manufactured and used by or for the Government for Government purposes without the payment of any royalties thereon or therefore.

The present disclosure is also made in the performance of work under a NASA contract and is subject to the provisions of Section 305 of the National Aeronautics and Space Act, Public Law 111-314, § 3 (124 Stat. 3330, 51 U.S.C. Chapter 201).

FIELD OF INVENTION

The present invention relates to systems for measuring human metabolic function and rates. More specifically, the present invention relates to a portable instrumented system that measures inhalation and exhalation airflow rates, heart rate and concentrations of carbon dioxide and oxygen in inhaled and exhaled breath.

BACKGROUND OF THE INVENTION

Measurements of a test subject's breathing rate, oxygen use rate, and production of carbon dioxide provide useful physiological data that can be used to gauge general health as well as the efficiency of the body in the utilization of dietary energy. Analysis of ventilation and pulmonary gas exchange provides a means for evaluating metabolic function under various circumstances of health and in the doing of physical work. Improvements and reduction in the size and weight of gas analyzers and computers have resulted in the appearance of a number of automated ventilation and pulmonary gas exchange analyzers. Such devices range from complicated laboratory systems requiring the use of powerful computers to simpler, less versatile systems for clinical use. Notably lacking among the prior art devices for metabolic measurement is the combination of portability and real-time data collection.

The most commonly measured variables are respiratory volume flow rate, oxygen consumption, carbon dioxide production, heart rate and respiratory exchange ratio, which is the ratio of carbon dioxide produced to oxygen consumed.

Earlier efforts directed towards respiratory gas analysis involve the timed collection of expired breath in rubberized breathing bags, measuring the volume collected, and analyzing the gas composition contained within. Metabolic rates were then calculated from the data. Obviously such a method was time consuming, non-portable, error-prone, and able to be performed only by well-equipped laboratories. Moreover, such methods were not suited to the measurement of short duration transients in metabolic functions.

One prior art solution was to record the relevant analog or digital data in a portable recorder, for later analysis.

At this time, there are tour companies that sell portable units for the measurement of metabolic parameters by means of the analysis of inhaled and exhaled air and heart rate. The four products are:

COSMED of Rome, Italy: Model-K4b2"

Medical Graphics Corp. of St. Paul Minn.: Model "V02000"

SensorMedics Corp of Yorba Linda, Calif.: Model "VmaxST

Erich JAEGER GmbH of Hochberg Germany Jaeger-Toennies: Model "Oxycon Mobile"

Each of these four portable systems employs relatively slow electrochemical sensor systems for oxygen analysis. Such 'wet chemistry' systems, in practice, operate at near their limits when driven at rates corresponding to human inhale/exhale rates. This means that the oxygen-sensor measurements must be corrected due to the relatively slow sensor lag times. The accuracy of these commercially available portable units is considerably less than large stationary metabolic carts used in hospitals. They also sample and analyze only a small portion of the exhaled air, rather than the entire volume of air that is inhaled and exhaled. Numerous studies were reviewed detailing operation of these four portable units compared to metabolic carts; such studies indicate that these types of commercial portable units typically have variable accuracy over the range of use, and yet they are considered to provide valuable approximations for field use outside of a clinical setting.

The COSMED model K4b2 appears to be covered by U.S. Pat. No. 4,658,832, to Brugnoli, with an assignment to COSMED, which is an Italian company. This '832 patent describes a portable system comprising a face mask that is fitted with a flow-measuring turbine and a what is called a "SLOW analyzer for oxygen concentration of a small portion, approximately 1%, of the exhaled breath. Metabolic activity is calculated on the basis of comparison of ambient oxygen concentration to exhaled oxygen concentration; exhaled carbon dioxide is not measured directly, but rather is inferred in the change in oxygen concentration between inhaled and exhaled air. Moreover, the oxygen concentration of exhaled air is based on averaging over one or more breaths. The device also uses a turbine to measure, or at least infers the exhaled airflow rate. The inertia of the turbine has to be taken into account during the end-of-breath phase of exhalation. Temporal resolution of this system is, at best, on a scale that is not less than that of a single inhalation/exhalation cycle.

The Medical Graphics model VO2000 seems to be covered by U.S. Pat. No. 6,554,776, to Snow, et al., assigned to Medical Graphics, said patent describing a portable method for measuring metabolism. This prior art invention uses a "bi-directional differential pressure Pitot tube" device called a "pneumotach" to measure inhaled and exhaled air-flow rates. The pneumotach device is described specifically in U.S. Pat. Nos. 5,038,773 and 5,119,825. The VO2000 product also employs a heart-rate monitor of the sort that utilizes multiple skin-mounted electrode pickups. The device extracts small gas samples from the pneumotach device, which are then measured for "oxygen uptake and carbon dioxide production . . . on a breath-by-breath basis" i.e., on a single-breath basis, and with, therefore, a single-breath degree of temporal resolution. The specific means by which oxygen and carbon dioxide are measured are not described in this method patent, but the diagrams suggest said means are remote from the test subject's mouth and nose. The anaerobic threshold is calculated on the basis of the average heart rate.

No specific U.S. Patent could be uncovered for the SensorMedics model VmaxST. However, U.S. Pat. No. 6,581,595 to Murdock, et al., and assigned to SensorMedics, a U.S. company, shows a simplified non-portable system that might utilize oxygen and carbon dioxide measurement methods that are similar in principle to those used in the portable VmaxST model. Further information on the VmaxST unit, including descriptive information, and a photograph, are at http://www.summittechnologies.ca/products/metabolics.htm. The model VmaxST includes a face mask and a radio-transmitting sending unit that is worn on the body of the test subject. The VmaxST diverts a small sample of exhaled gas, which is analyzed remotely from the face. Oxygen concentration is measured with by means of an electro-chemical cell, which has an intrinsic rime delay, and CO2 is measured by means of IR absorption, also remote from the face of the test subject. The unit has single-breath temporal resolution. Heart rate is measured with ECG electrodes.

No specific U.S. Patent could be uncovered for the fourth portable unit listed above, the model Oxycon Mobile made by Jaeger-Toennies. However, a manufacturer's brochure, in *.pdf format, is available from V1ASYS Healthcare Inc., located at 22745 Savi Ranch Parkway in Yorba Linda, Calif. 92887-4668. The device shown in the brochure comprises a face mask to which a non-turbine type flow-rate measurement device incorporates a single tube that carries a portion of the inhaled and exhaled gases to a back-worn analyzer and transmitter having a range of 1,000 meters. Heart rate is measured with optional 3- or 12-lead ECG pickups. The methods of gas analysis are not specified, but the brochure implies that both carbon dioxide and oxygen concentrations are measured, albeit from only a portion of the exhaled gas. The descriptive brochure does not mention high data rates, which suggests that the device's temporal resolution is on the order of a single breathing cycle.

SUMMARY OF THE INVENTION

According to the present invention, there is disclosed a portable unit for metabolic analysis of a test subject. The portable unit includes a mask adapted for covering the test subject's mouth and nose. The mask has a manifold portion which bifurcates into first and second manifold flow channels that are open at their free ends and is adapted for conveying inhaled and exhaled air to and from the test subject A carbon dioxide (CO2) sensor subsystem is disposed in the first manifold flow channel. An oxygen sensor subsystem is disposed in the first manifold flow channel. An airflow rate sensor is disposed in the second manifold flow channel. A computer is connected to the carbon dioxide sensor subsystem, the oxygen sensor subsystem, and the airflow rate sensor for receiving data signals from the carbon dioxide sensor subsystem, the oxygen sensor subsystem, and the airflow rate flow sensor and for digitizing the data signals into digitized data and wirelessly conveying the digitized data to another computer which stores the digitized data for display and analysis.

Also according to the present invention, the carbon dioxide sensor subsystem has an inner support housing, an intermediate support housing and an outer support housing, and the intermediate support housing forms an air flow channel that is part of the flow manifold through which the air being inhaled and exhaled by the test subject passes.

Further according to the present invention, a plurality of infrared light-emitting diodes are mounted onto an interior surface of the inner support housing to project IR energy through the air flowing through the air flow channel of the intermediate support housing.

Still further according to the present invention, a sapphire window is disposed between the intermediate support housing and the inner support housing for separating the infrared light-emitting diodes from the air flow channel. A photo detector is mounted in the outer support housing; and a narrow-band-pass filter is disposed between the outer support housing and the intermediate support housing across the airflow channel from sapphire window to allow a selected bandwidth of the IR energy from the LEDs to pass through to photo detector. Each of the LEDs is positioned to direct their energy at the photo detector. The LEDs are driven at about 1.0 to about 2.0 amps and in pulses having a duty cycle of about 0.01 to about 0.1 percent. The photo detector is situated upon a thermoelectric cooling device which conveys heat to a heat-dissipating fin assembly.

Yet further according to the present invention, the oxygen-sensing subsystem is located in the flow manifold with the $CO_2$ subsystem. The oxygen-sensing subsystem has a lower removable housing, an intermediate housing including an enclosed cylinder which is integral with manifold flow channel and an upper housing. The oxygen-sensing subsystem includes: an optic fiber for conveying a blue laser light into the lower housing of oxygen sensor; and a collimating optics system for directing the blue light across the air passing through enclosed cylinder and being sampled for oxygen concentration of the air being inhaled and exhaled by the test subject and into a support disk having a layer of ruthenium based, oxygen-quenched fluorophore dye disposed thereon and mounted in the upper housing. The collimating optics system includes a mirror and first, second and third lenses which are held within removable housing. Orange light is reflected back to a detector disposed within the box by way of the optics system and the optic fiber. The blue laser light is sinusoidally intensity-modulated at 40 kHz, whereby the resulting orange fluorescence from the excited fluorophore dye layer is phase-shifted relative to incident blue light.

According to the present invention, the oxygen sensor subsystem includes a temperature measuring device located near the oxygen sensitive dye layer in the upper housing to and connected to the computer to measure the temperature of the air being inhaled and exhaled by the test subject. The temperature measuring device is selected from the group consisting of a thermocouple and a resistive temperature sensor.

Further according to the present invention, airflow rate sensor is an ultrasonic flow sensor that measures the inhalation and exhalation flow rates of the test subject within the one manifold flow channel. The airflow rate sensor measures a flow rate measurement of about 200 liters per minute in the single manifold flow channel.

Also according to the present invention, a pressure transducer measures ambient air pressure.

Yet further according to the present invention the portable unit includes a heart-rate monitor adapted to send an output signal to the computer.

According to the present invention, a method of making a metabolic analysis of a test subject, comprises the steps of: covering the test subject's mouth and nose with a mask having a manifold portion which bifurcates into first and second manifold flow channels that are open at their free ends whereby inhaled and exhaled air can be conveyed to and from the test subject; measuring the carbon dioxide level of the inhaled and exhaled air being conveyed to and from the test subject with a carbon dioxide sensor subsystem disposed in the first manifold flow channel; measuring the oxygen level of the inhaled and exhaled air being conveyed to and from the test subject with an oxygen sensor subsystem disposed in the first manifold flow channel; measuring the airflow rate of the inhaled and exhaled air being conveyed to and from the test subject with an airflow rate sensor disposed in the second manifold flow channel; generating digitized data from data signals received from the carbon dioxide sensor subsystem, the oxygen sensor subsystem, and the airflow rate sensor and the airflow rate flow sensor; and storing the digitized data for display and analysis.

Also according to the present invention, the method includes the step of generating digitized data from data signals received from the carbon dioxide sensor subsystem, the oxygen sensor subsystem, and the airflow rate sensor and the airflow rate flow sensor in a first computer carried by the test subject. The method also includes the step of wirelessly conveying the digitized data to a second computer which stores the digitized data for display and analysis.

According to the present invention, a carbon dioxide sensor for sensing the level of carbon dioxide in air being inhaled and exhaled by a test subject, comprises: an inner support housing; an outer support housing; an intermediate support housing forming an air flow channel through which the air being inhaled and exhaled by the test subject passes; and a plurality infrared light-emitting diodes being mounted onto an interior surface of the inner support housing to project IR energy through the air flowing through the air flow channel of the intermediate support housing. A sapphire window is disposed between the intermediate support housing and the inner support housing for separating the infrared (IR) light-emitting diodes from the air flow channel. A photo detector is mounted in the outer support housing and a narrow-band-pass filter is disposed between the outer support housing and the intermediate support housing across the airflow channel from sapphire window to allow a selected bandwidth of the IR energy from LEDs to pass through to photo detector. The photo detector is situated upon a thermoelectric cooling device which conveys heat to a heat-dissipating fin assembly. Each of the LEDs positioned such that they all aimed to direct their light at the photo detector. The LEDs are driven at about 1.0 to about 2.0 amps and in pulses having a duty cycle of about 0.01 to about 0.1 percent.

Further according to the present invention, an oxygen-sensing subsystem for sensing the level of oxygen concentration in air being inhaled and exhaled by a test subject, comprises a lower removable housing; an intermediate housing including an enclosed cylinder forming an air flow channel through which the air being inhaled and exhaled by the test subject passes; an upper housing; an optic fiber for conveying a blue laser light into the lower housing of oxygen sensor, and a collimating optics system for directing the blue light across the air passing through enclosed cylinder and into a support disk having a layer of ruthenium-based, oxygen-quenched fluorophore dye disposed thereon and mounted in the upper housing. The collimating optics system includes a mirror and first, second, and third lenses which are held within removable housing. A photo detector is provided to which orange light reflects back to by way of the optics system and the optic fiber. The blue laser light is sinusoidally intensity-modulated at 40 kHz, whereby the resulting orange fluorescence from the excited fluorophore dye layer is phase-shifted relative to incident blue light.

A temperature measuring device is located near the oxygen sensitive dye layer in the upper housing to measure the temperature of the air being inhaled and exhaled by the test subject. The temperature measuring device is selected from the group consisting of a thermocouple and a resistive temperature sensor.

BRIEF SUMMARY OF THE DRAWINGS

The structure, operation, and advantages of the present invention will become further apparent upon consideration of the following description taken in conjunction with the accompanying figures (Figs.). The figures are intended to be illustrative, not limiting.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

Figure 1:
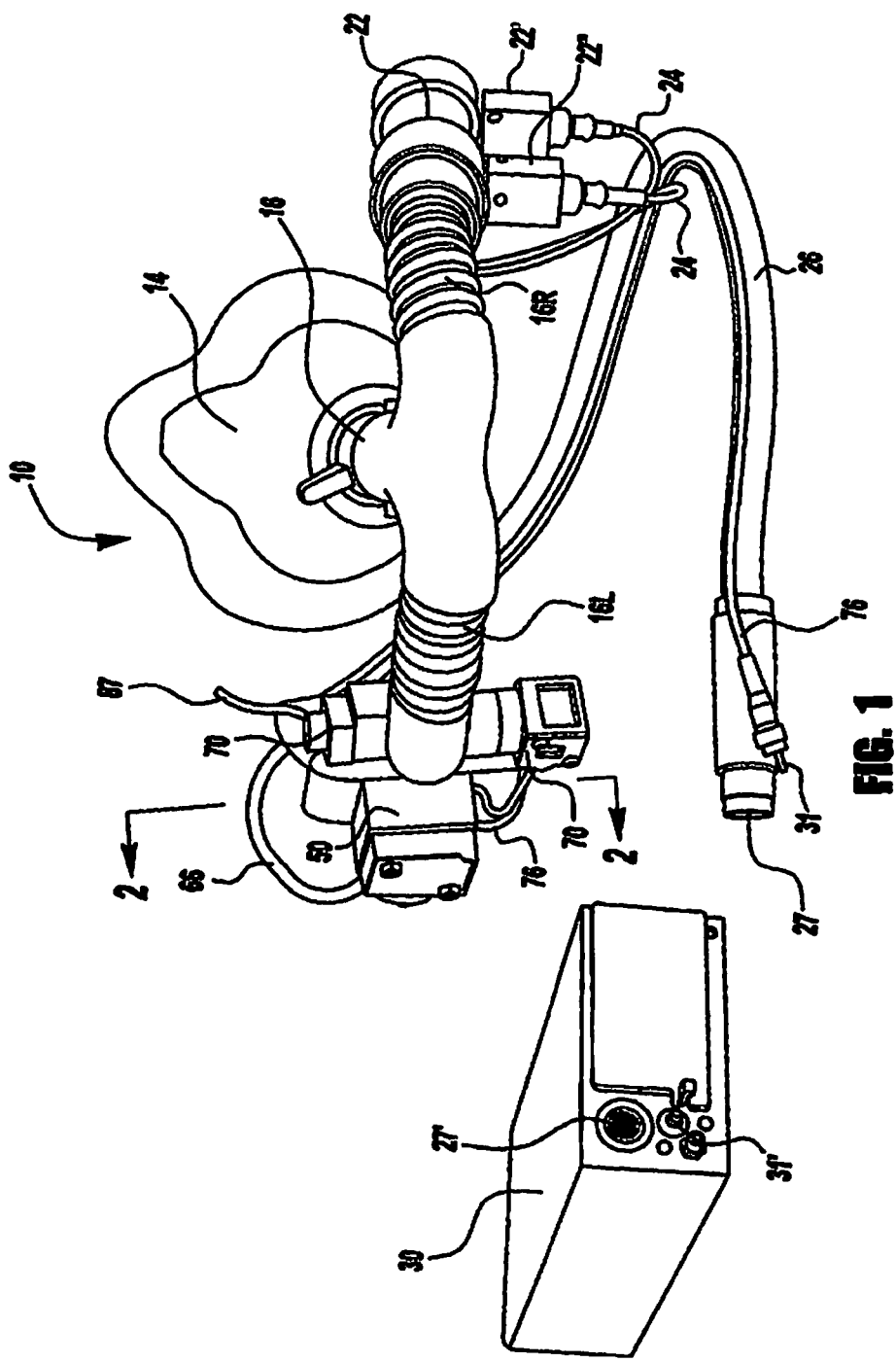

In the drawings accompanying the description that follows, often both reference numerals and flow channel ends (labels, text descriptions) may be used to identify elements. If flow channel ends are provided, they are intended merely as an aid to the reader, and should not in any way be interpreted as limiting.

Figure 1A:
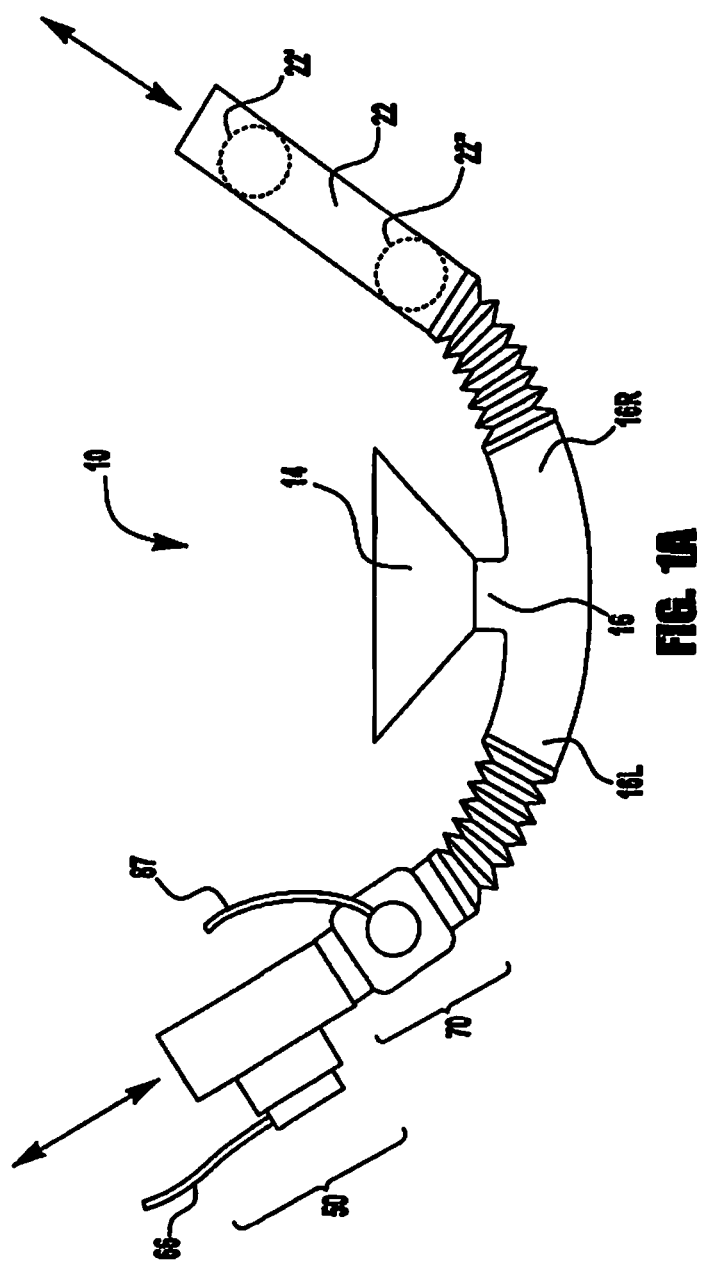

FIG. 1 is a front isometric view of the present invention;

FIG. 1A is a top view of the essential element

Figure 2:
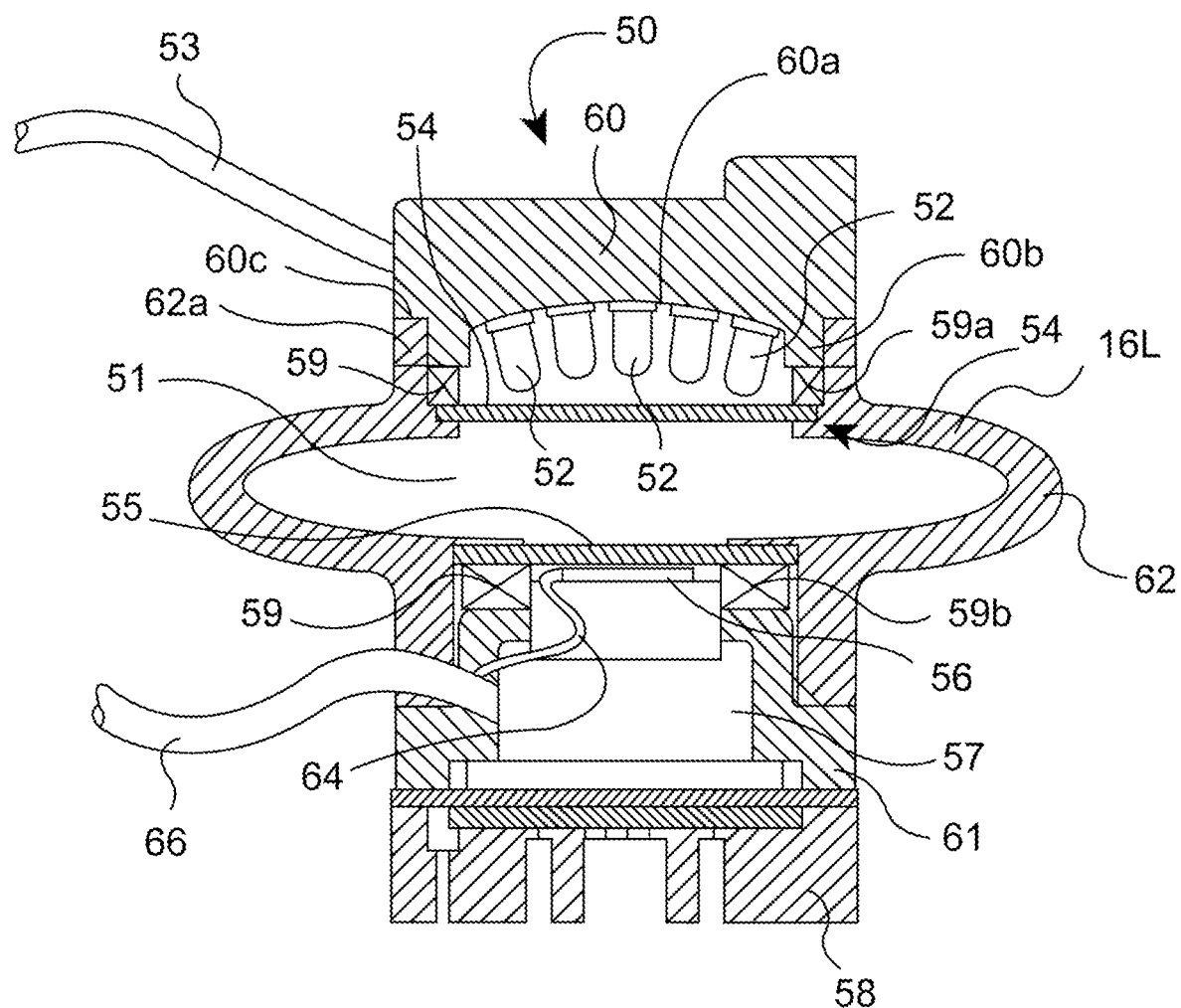
Figure 3:
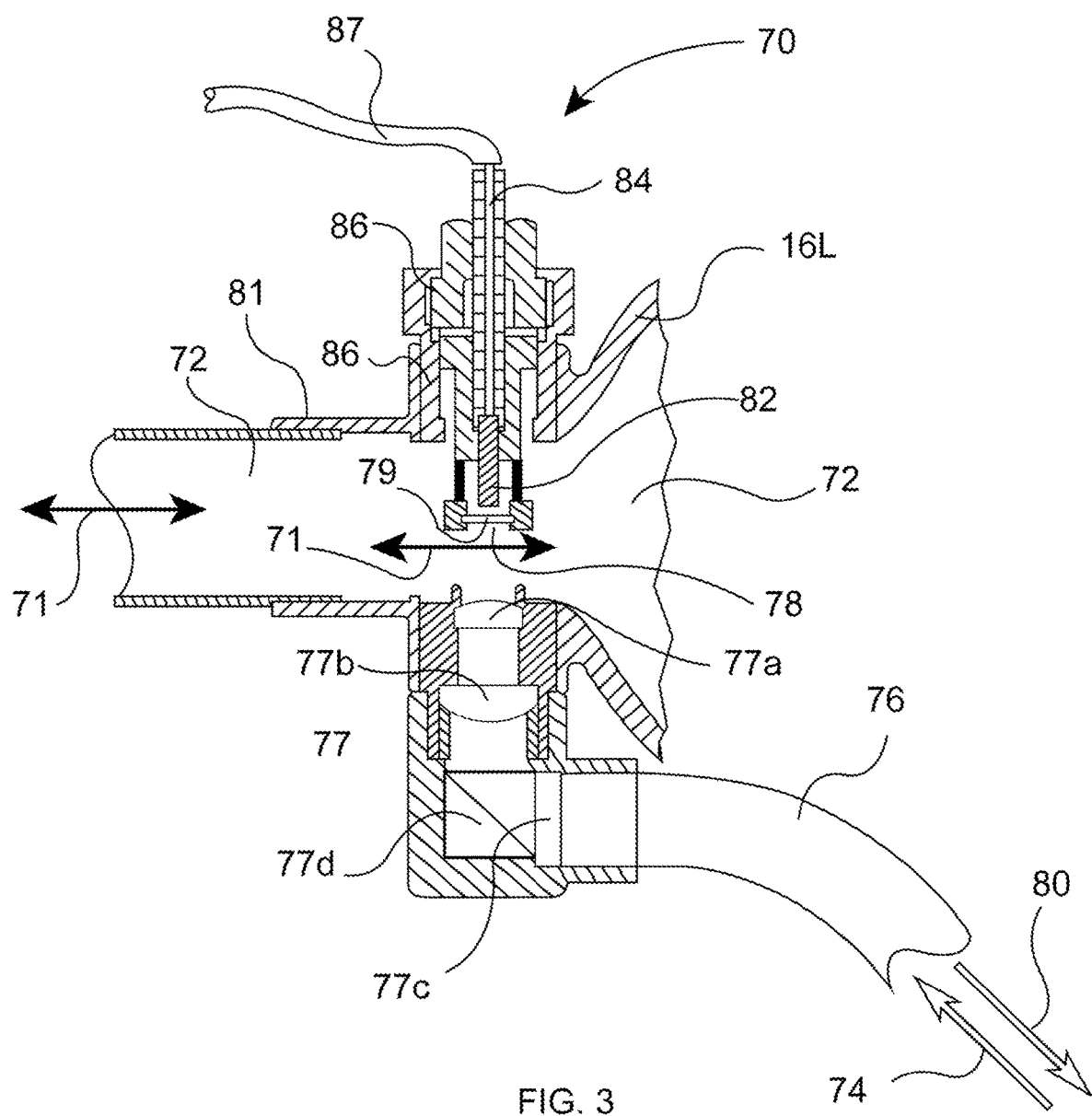
Figure 4:
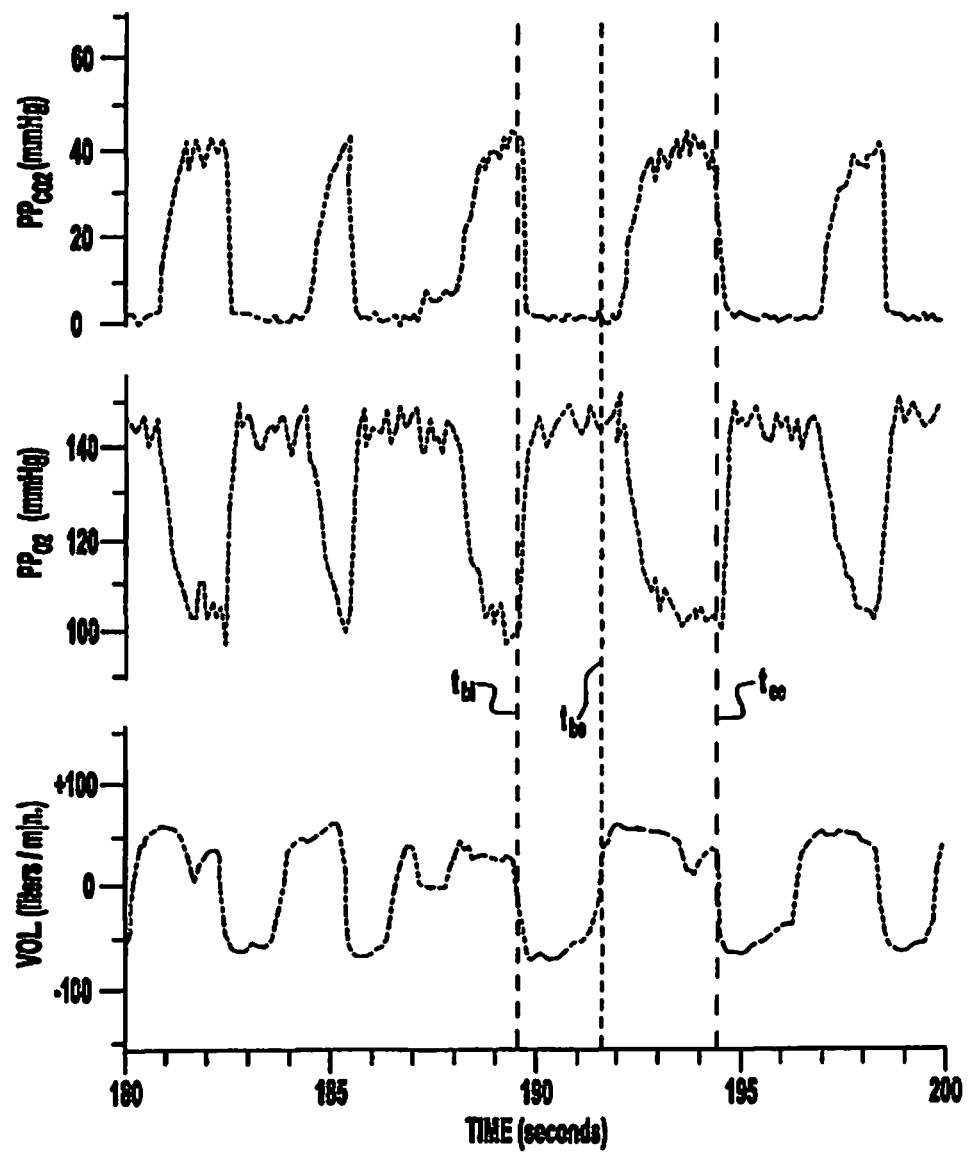

FIG. 2 is a schematic cross-sectional view of the carbon-dioxide-concentration measuring subsystem portion of the present invention;

FIG. 3 is a schematic cross-sectional view of the oxygen-concentration measuring subsystem portion of the present invention;

FIG. 4 is a representation of metabolic data taken from a human test subject.

Figure 5:
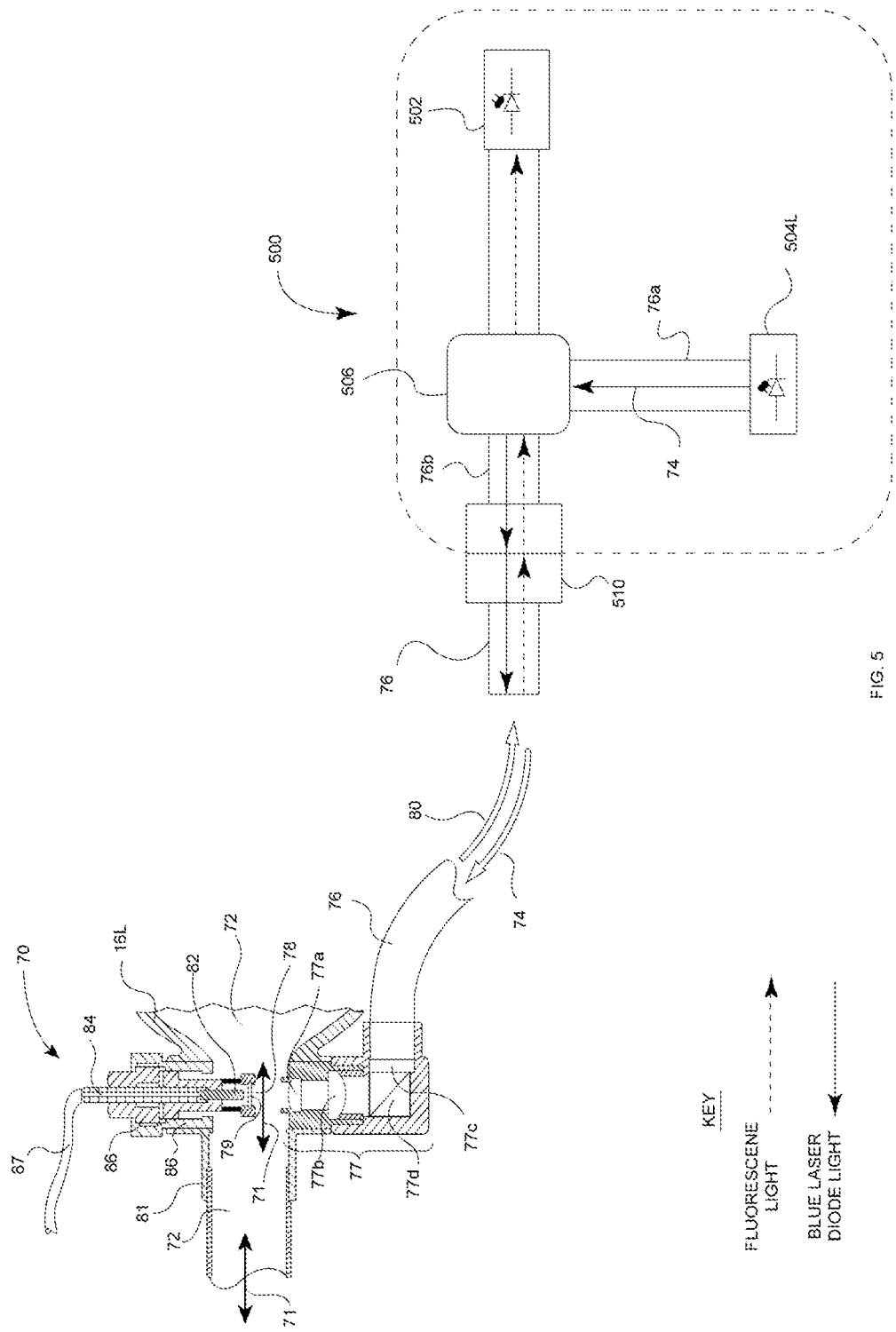
Figure 6:
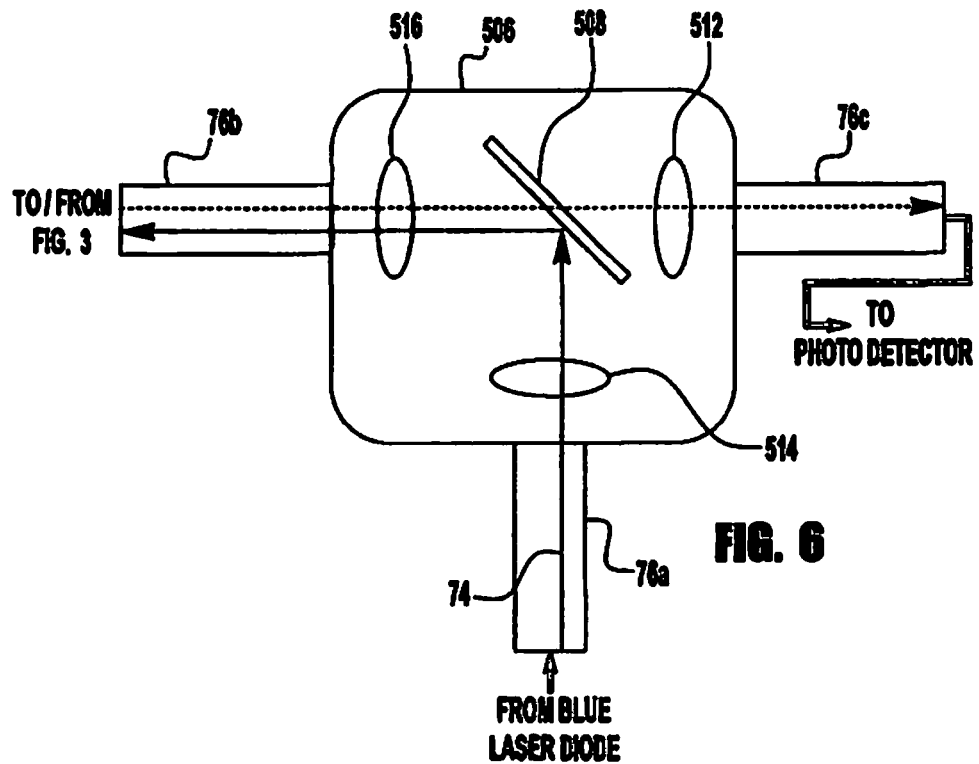
Figure 7:
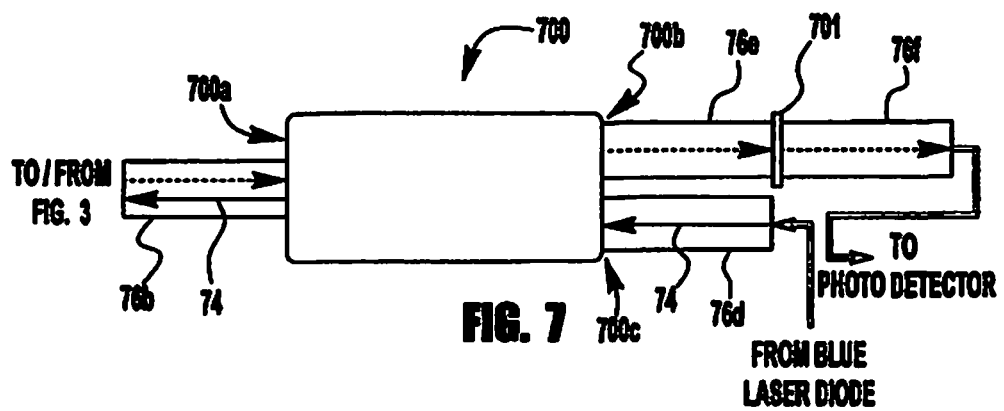

FIG. 5 is a schematic view of the oxygen-concentration measuring subsystem portion typically disposed in the electronics box of the present invention;

FIG. 6 is a schematic view of the optical filtering system portion of the oxygen-concentration measuring subsystem of FIG. 5; and FIG. 7 is a schematic view of an alternative embodiment of an oxygen-concentration measuring subsystem portion typically disposed in the electronics box of the present invention.

DETAILED DESCRIPTION OF THE PREFERRED EMBODIMENTS

FIG. 1 is a representational frontal isometric view of a Portable Unit for Metabolic Analysis (a.k.a. PUMA) 10 adapted to be attached to the face of a human test subject. The PUMA unit 10 comprises a standard face mask 14 of the sort that is adapted to cover the test subject's mouth and nose. While the mask is illustrated as completely covering the test subject's mouth and nose, it is also within the terms of the invention to simply use a mouthpiece and nose clip. The nose clip eliminates breathing through nose and directs all inhale/exhale flow from the mouth to PUMA 10. Within the terms of the present application, the face mask 14 includes either the mask as shown or a mouthpiece and nose clip. The mask 14 has a manifold portion 16 which bifurcates into two flow channels 16L and 16R, which convey inhaled and exhaled air to and from the test subject 12.

As shown in FIGS. 1 and 1A, flow channel 16L contains a conduit with a carbon dioxide (CO*) sensor subsystem 50 and an oxygen (O2) sensor subsystem 70. Flow channel 16R has a conduit with an ultrasonic flow sensor 22 which includes two transducers 22' and 22". Wires 24 from the transducers 22' and 22" lead to a larger cable 26 that communicates with a small digitizing and transmitting computer (not shown) disposed within electronics box-like structure 30. The large cable 26, with plug 27 at its distal end, plugs into a port 27 of the box-like structure 30 and thereby communicates with the digitizing computer, conveying data thereto from the aforementioned sensors for oxygen, carbon dioxide, and airflow rate. NOTE: A fiber optic line 76 is contained within the cable bundle 26 and has a terminal connector 31 which connects with the socket 3 P on the box 30 that also contains the digitizing computer. A blue laser light, as explained below, causes a dye inside of the oxygen sensor 70 to fluoresce in a color different from blue, such as orange. The fluorescent light is also conveyed through the same optic fiber 76 from the oxygen sensor 70 to the box 30 that contains a means to measure the oxygen-proportional phase shift (relative to the blue laser light) of the light that has been excited to fluorescence by the blue laser light that travels in the optic fiber. Heart rate is measured separately by means of a heart-rate monitoring band (not shown) that is worn around the chest of the test subject. The heart rate sensor can be a wireless heart rate sensor with a receiver mounted adjacent to the flow sensor (22). For example, the heart rate receiver can be made by Polar Corp. The heart-rate data is also fed into the digitizing computer by means of the cable 26 with plug 27 and socket 27'. The small box 30 is carried upon the person of the test subject when the PUMA invention is being used. The computer digitizes the data signals from the aforesaid sensors and wirelessly conveys the digitized data to a desktop or laptop computer (not shown) which in turn stores the digitized data for display and analysis. In addition to the raw data (air temperatures, pressure, flow, oxygen and carbon dioxide mole fraction, heart rate), the inventors intend that the computer display will further include (but not be limited to) volumetric oxygen consumption, volumetric carbon dioxide production, respiratory equivalent ratio and volumetric flow rate of exhaled gas.

Referring to FIG. 1 A, as the test subject breathes in and out, air moves in both directions, as shown by the arrows, within flow channels I6L, 16R of the manifold 16 of the mask 14. The flow sensor 22 in the flow channel I6R measures the airflow speed, and thus air flow rate during inhalations and exhalations, in the flow channel 16R only. Flow impedance of each flow channel 16,16R is constant, so that the airflow sensor 22 in the flow channel 16R is able to measure an airflow rate that can be calibrated so as, effectively, to determine for the sum of the inhalation and exhalation flow rates in both manifold flow channels.

The metabolic parameters of specific interest are air pressure and temperature, inhaled and exhaled airflow rates, heart rate, and the partial pressures of inhaled and exhaled oxygen and carbon dioxide.

Commercial, off-the-shelf technology that is described in more detail hereinbelow is used to measure air pressure and temperature, and airflow rate. Measurements of the partial pressures of inhaled and exhaled oxygen and carbon dioxide are done by means of hardware developed at the NASA Glenn Research Center. Each measurement subsystem of the present invention is described in detail below.

Carbon Dioxide Measurement Subsystem

FIG. 2 is a schematic, cross-sectional top view of the carbon dioxide sensor subsystem 50 through line 2-2 of FIG. 1, showing the air flow channel 51, within the flow channel 16L, as perpendicular to, or coming into and out of the page of FIG. 2. Sensor 50 has an inner support housing 60, an intermediate support housing 62 and an outer support housing 61. The intermediate support housing 62 forms the air flow channel 51 and is part of the flow manifold 16L. The inner support housing 60 has a curved interior surface 60a formed between upright end wall 60b which in turn forms a collar 60c.

A plurality infrared (IR), light-emitting diodes (LEDs) 52 are mounted onto the curved interior surface 60a to project IR energy through the air flowing through the air flow channel 51 of intermediate support housing 62. Although an array of eight infrared (IR) light-emitting diodes (LEDs) 52 are shown, it is within the scope of the present invention to use any desired number of LEDs. A plurality of individual LEDs 52 (made by Ioffe in St. Petersburg Russia) are used in constructing the exemplary array of LEDs 52 as shown. The intermediate support housing 62 has an inner end 62a that is secured against the upright end wall 60b and the collar 60c of the inner support housing 60. A sapphire window 54 is mounted between the inner end 62a of the intermediate support housing 62 and the upright end wall 60b of the inner support housing 60. A gasket 59a disposed between intermediate support housing 62 and inner support housing 60 maintains the IR sapphire window 54 in place. The sapphire window 54 separates the infrared (IR) light-emitting diodes (LEDs) 52 mounted onto the curved interior surface 60a from the air flow channel 51 and isolates the LEDs from humidity and moisture in the inhaled and exhaled gas, i.e. the user's breath.

The sapphire window 54 can have an anti-fog coating applied the surface within airflow channel 51 to eliminate the effects of condensation during exhalation.

The IR energy, after passing through sapphire window 54 propagates through the airflow channel 51 to a narrow-band-pass filter 55 mounted between the outer support housing 61 and the intermediate support housing 62 across the airflow channel 51 from sapphire window 54. A gasket 59b disposed between intermediate support housing 62 and outer support housing 61 maintains filter 55 in place. The narrow-band-pass filter 55 allows a selected bandwidth of the IR energy from LEDs 52. i.e., 4.25 to 4.44 microns to pass through to a photo detector 56 mounted in the outer support housing 61. The photo detector 56 is situated upon a thermoelectric cooling device 57 which conveys heat to a heat-dissipating fin assembly 58.

The LEDs 52 of the array are positioned such that they are all aimed to direct their light at the detector 56. For example, LEDs 52 are arranged such that seven of the LEDs are arranged in a circle around a single central LED. Each LED has a lens to collimate its output. Each of the eight LEDs 52 are rated at greater than 120 microwatts peak when driven at 1 amp, but in this invention they are driven at about 1.0 to about 2.0 amps and preferably about 1.3 to about 1.6 amps and most preferably about 1.5 amps and in pulses having a duty cycle of about 0.01 to about 0.1 percent and preferably about 0.02 to about 0.06 percent and most preferably about 0.04 percent If the LEDs 52 are driven at more than about 0.1 percent, then the life of the LEDs will be significantly reduced. If the LEDs 52 are driven at less than 1.0 amps then the intensity of the IR energy will not be sufficient to be measured accurately by the photo detector (56). If the LED pulse width is less than 10 µsec, the pulsing circuitry powering the LEDs will have insufficient time to provide a stable output to the LEDs. Accordingly, if the pulse width is shorter than 10 µsec, the Infrared energy from the LEDs will not be constant and the accuracy of the measurement will decrease. The on-board microprocessor acquires the electrical signal from detector 56 approximately 10 µsec after the ON pulse is sent to the LED array to allow the pulsing circuitry powering the LEDs to stabilize.

The filter 55 has its peak transmission at 4.350 microns and has a full width, half max of 0.18 microns. Power cable 53 conveys power to the IR LED array 52 that is mounted within the housing 60. Wire 64 conveys voltages from photo detector 56 into the cable 66 which also carries power, of about 0.25 watts, to the thermoelectric cooling device 57. An exemplary detector 56 is a passive photovoltaic Mercury Cadmium Telluride (HgCdTe) detector manufactured by Judson Technologies. The thermoelectric cooling device 57 serves the dual purpose of stabilizing the response of the detector 56 and increasing its sensitivity.

Measurements of the carbon dioxide partial-pressures are achieved by means of a relatively sharp IR absorption line for carbon dioxide at a wavelength of about 4.2 to about 4.5 microns and preferably about 4.3 microns. The wavelength is chosen because it is unaffected by variations in the concentration of water vapor in the air stream that moves within the flow channel 51 of manifold flow channel 16L. Relatively broad-band IR energy from LEDs 52 traverses the Alter 55 before striking the IR sensor 56. The inhale/exhale airstream passes between the IR source 52 within the housing 60 and the HgCdTe photo detector 56, thus attenuating the 4.3 micron (μ) portion of the IR energy from the LED array 52.

The CQ2 subsystem 50 uses the absorption feature located at the 4.3 um wavelength. The LEDs 52 are pulsed at about 5 to about 15 Hz and preferably at about 10 Hz and at a low duty cycle so as to minimize the amount of heat that is conveyed to the detector 56.

The main reason for pulsing LEDs 52 is to minimize the heat buildup in the LEDs and prolong their lives. However if the LEDs 52 were on continuously, they would heat up the detector 56. The ON duty cycle is about 0.01 to about 0.1 percent and preferably about 0.02 to about 0.06 percent and most preferably about 10 percent of the complete ON pulse of the LEDs 52.

Oxygen Measurement Subsystem

FIG. 3 is a cross-sectional, schematic side view of the oxygen-sensing subsystem 70 located in the flow manifold 16L, preferably upstream from the CO2 subsystem 50. The subsystem 70 has a lower housing 77, an intermediate housing 81 and an upper housing 86.

During inhalation and exhalation of a test subject, air flows bidirectionally, according to the double-headed arrows 71, within the enclosed cylinder 72 of intermediate housing 81, which is integral with manifold flow channel 16L of FIG. 1.

The oxygen partial pressure measurement subsystem 70 utilizes the fluorescence oxygen-quenching properties of a Ruthenium-doped organic dye, such as tris(4,7-diphenyl-1,10-phenanthroline) ruthenium (II) perchlorate, as describe by Bacon, et al$_M$ in U.S. Pat. No. 5,030,420. The excitation source is a blue laser diode (not shown), the blue light 74 of which is conveyed into the lower housing 77 of oxygen sensor 70 by way of an optic fiber 76. The blue light 74 traverses the collimating optics set which includes mirror 77d and lenses 77a, 77b, and 77c and are held within removable housing 77. After the blue light is transmitted through lens 77a, it crosses the air held in cylinder 72 and is directed into a thin support disk 78 mounted in the upper housing 81.

A thin layer 79 of ruthenium-based, oxygen-quenched fluorophore dye is disposed upon the flat, thin support sensing disk 78, across which the air being sampled for oxygen concentration passes during the inhalation/exhalation of the test subject. Orange fluorescent light (excited by the blue laser light) of the ruthenium-based fluorophore dye layer 79 is "quenched" to a degree that is directly related to the concentration of oxygen that comes into contact with the dye layer. The orange light 80 reflects back to a oxygen measurement subsystem 500 by way of the same optics system 77d, 77c, 77b, and 77a to optic fiber 76 as is used by the incoming blue laser light 74. The oxygen measurement subsystem 500, shown in FIGS. 5 and 6, is shown in incorporated in the box 30 that holds the digitizing computer. The oxygen-concentration measuring detector system 500 (see FIGS. 5,6, and 7) which measures the intensity of the orange light 80, and its phase shift relative to the blue light, is contained within the same box 30 that holds the digitizing computer. That is to say, the fiber optic line 76 conveys blue light from a laser diode source that is disposed within the box 30 (see FIG. 1) to the oxygen sensor subsystem 70. The fiber optic line 76 also conveys the return light signal of what is shown here as orange light 80 back to a photo detector 502 that is also disposed within the detector system 500 provided in electronics box 30.

The fluorophore dye is the basis of a commercial product that measures gaseous and dissolved oxygen concentrations within a fluid (liquid or gas). When excited to fluorescence by blue light, the specific dye used by the inventors thus far fluoresces orange light. Oxygen quenches the fluorescence process to a degree is related to the concentration of oxygen that makes contact with the dye layer 79. The oxygen subsystem 70 uses Ocean Optics probe tips 79, but operates in a manner that has been modified from that supplied by Ocean Optics. The laser diode (not shown, though disposed within the box 30 in FIG. 1) is sinusoidally intensity-modulated at 40 kHz. The resulting orange fluorescence from the excited fluorophore dye layer 79 is phase-shifted relative to the incident blue light.

The oxygen sensor subsystem 70 also includes a thermocouple or resistive temperature sensor 82 in the upper housing whose voltage is conveyed to the computer 30 by way of electrical lead 84 which is secured within the support housing 86. In some embodiments, there is a voltage reference that provides a constant voltage to the resistive temperature sensor connected to a voltage divider network. The microprocessor measures the voltage across the divider network to determine the temperature. The electrical lead 84 from the resistive temperature sensor 82 is connected to cable 87, which conveys the resistance of the resistive temperature sensor to the main cable 26 (FIG. 1). The resistive temperature sensor 82 measures the temperature of the air being inhaled and exhaled. Temperature measurement by means of the resistive temperature sensor 82 is a critical element to the calibration of the oxygen sensor 70, which is why the resistive temperature sensor 82 is located close to the oxygen sensitive dye layer 79 on the thin surface 78. An exemplary resistive temperature sensor 82 is made by Thermometries. However it is within the scope of the invention for the element 82 to be a thermocouple.

Referring to FIGS. 5 and 6, there is illustrated a schematic view of the oxygen-concentration measuring subsystem portion 500 typically disposed in the electronics box 30 of the present invention. The oxygen-concentration measuring subsystem portion 500 is secured to one end of the multimode optical fiber 76 by an optic connector box 510. A blue light 74 from a blue light source laser diode 504 is directed through a multimode optical fiber 76a through a lens 514, onto an optical filtering system 508, then through a lens 516, into the multimode optical fiber 76b, into multimode optical fiber 76, across the collimating optics set, through the air in cylinder 72 and onto the sensing disk 78.

The sensing disc 78 then fluoresces and the light propagates back through the fiber 76, through a lens 516 and through an optical filter 508. The optical filter 508 removes any remaining blue light from the orange light before going through a lens 512, a optical fiber 76c and to a photo detector 502. Finally the orange light reaches a photo detector 502. The signal received at the photo detector 502 is compared to the signal used to drive the laser diode 504.

FIG. 6 is a schematic view of the optical filtering system portion of the oxygen-concentration measuring subsystem of FIG. 5. During operation of the oxygen sensor subsystem 70, the PUMA electronics system within box 30 measures the phase-shift between the incident blue 74 and fluorescence orange 80 signals. The electronics and optics of the oxygen sensor subsystem 70 work as follows. A 40 kHz signal is generated and fed to a laser diode driver. The laser diode driver in turn drives the blue laser diode, 504, at 40 kHz. The light from the blue laser diode 504 propagates through a multimode optical fiber 76a through a lens 514 then reflects off an optical filter 508 and through lens 516, then through the multimode optical fiber 76b, into multimode optical fiber 76, across the collimating optics set, through the air in cylinder 72 and onto the sensing disk 78. The sensing disc 78 then fluoresces and the light propagates back through the fiber 76, through a lens 516 and through an optical filter 508. The optical fitter 508 removes any remaining blue light from the orange light before going through a lens 512, a optical fiber 76c and to a photo detector 502. The signal received at the photo detector 502 is compared to the signal used to drive the laser diode 504. The phase shift between these two signals is what is correlated to any oxygen concentration. The degree of phase-shift correlates with the oxygen partial pressure within the flow of gas in the duct 72. In order to minimize photo-bleaching of the fluorophore, the PUMA unit is designed to gate the blue laser diode at 10 Hz, with about a 10% duty cycle.

Referring to FIG. 7, there is shown a schematic view of an alternative design of an oxygen-concentration measuring subsystem portion 700 typically disposed in the electronics box 30 of the present invention. The alternate electronics and optics of the alternate oxygen-concentration sensor subsystem 700 work as follows. A 40 kHz signal is generated and fed to a laser diode driver. The laser diode driver in turn drives the blue laser diode, 504, at 40 kHz. The blue laser light 74 propagates through multimode optical fiber 76d then through multimode optical coupler 700. The blue laser light exits multimode coupler 700 at port 700a and propagates through multimode optical fiber 76b, then into multimode optical fiber 76, across the collimating optics set, through the air in cylinder 72 and onto the sensing disk 78. The sensing disc 78 then fluoresces and the light propagates back through the fiber 76 and 76b, to port 700a of multimode optical coupler 700. The fluorescence exits multimode coupler 700 at port 700c and 700d. The light at 700c is ignored. The light exiting port 700b propagates though multimode optical fiber 76e to optical filter 701 where any remaining blue laser diode light is removed. The fluorescence light then propagates through optical fiber 76f to a photo detector 502. As in the embodiment shown in FIGS. 5 and 6, the signal received at the photodiode is compared to the signal used to drive the blue light source laser diode. The phase shift between these two signals is what is correlated to the partial pressure of oxygen at the probe tip 78.

Airflow Measurement Subsystem

The airflow rate sensor 22 (FIG. 1) of the invention 10 is a modified version of a commercial ultrasonic flow sensor manufactured by Gill Instruments Limited, in Lymington, England. The flow sensor 22 measures inhalation and exhalation flow rates within the one manifold flow channel 16R shown in FIG. 1 but, as described below, suffices to measure the airflow rate in both flow channels I6LJ6R of the manifold 16. The air-flow rate measurement device 22 is able to measure total flow rates of up to 400 liters per minute, as inferred for both manifold flow channels 16L, 16R, instead of the design maximum flow-rate measurement of 150 liters per minute.

Part of the increased flow rate measurement derives from the bifurcated nature of the manifold 16 (FIGS. 1 and 1 A) whereby the constant flow impedance of each manifold 16L and I6R enables the flow measurement of one manifold (I6R in FIGS. 1 AND 1 A) to be used as a basis for inferring the total flow of both manifold portions 16J6R. Note that the flow split between manifold portions I6J6R need not be equal. The impedance just needs to be constant so the total flow can be deduced or measured from the flow measurement Part of the modification of the original Gill instrument entails a recalibration of the output variables from the transducers 22', 22", so as to allow a flow rate measurement of approximately 200 liters per minute in the single manifold flow channel I6R, and a 400-liter-per-minute total flow rate to be inferred for both flow channels 16L, 16R of the system 10. Another modification from the original Gill instrument design is that the signals from the transducers 22', 22" are calibrated within the digitizing computer contained in box 30 (FIG. 1), rather than within a unitary transducer plug-in device that is supplied as part of the original Gill instrument package.

The Gill ultrasonic flow velocity device 22 acquires data at a rate of 10 Hz.

Pressure and Temperature

The PUMA invention 10 uses a commercial, off-the-shelf (COTS) miniature diaphragm-type pressure transducer to measure ambient air pressure which, though originally housed within the manifold portion 16 or one of the flow channels 16L, I6R thereof, is housed within the box 30 that holds the digitizing computer. Human testing of the invention has shown that pressure within the manifold flow channels 16L, 16R varies minimally during inhalation and exhalation, and that, therefore, the pressure transducer needs only to provide a measure of the ambient air pressure.

Heart Rate Monitor Subsystem

The PUMA unit uses a COTS heart-rate monitor, such as a heart-rate monitor made by Polar Corp. The receiver for the heart rate sensor is located adjacent to the flow sensor (22). It is unmodified, except that its output signal is integrated with the PUMA electronics located in the computer box 30. The Polar transmitter is of the chest strap type. The heart rate data is supplied to the computer 30 in the form of a pulse every heart beat. The heart rate receiver board outputs a digital pulse every time it detects a heart beat. The PUMA acquisition and control electronics system located in box 30 then computes a heart rate from the counts (pulses) that it outputs wirelessly to the external computer at 10 Hz (along with the other data).

Acquisition and Control Electronics

The digitizing computer, and the acquisition and control electronics in housing box 30 of the present PUMA invention, are electronically and optically tethered to the sensor electronics and optics located on the mask 14 by means of the cable 26 and optic fiber 76 shown in FIG. 1. The computer is battery powered and capable of being worn during exercise. The battery for powering the system can be a 7.2-volt, lithium-ion Canon camcorder battery having a 3,000 mA-hour capacity. The computer contains all of the electronics necessary to control all of the PUMA sensors described herein above. It digitizes all of the signals from the sensors and acquires sensor data at 10 Hz. In order to do this, the electronic package digitizes the signals from the $O_2$ and $CO_2$ subsystems at a much higher rate in order to extract the partial pressure information. The software for the acquisition and control computer is custom-developed in C++.

The computer shares the same housing box 30 as contains the blue laser diode and other optics features and light-intensity measurement systems and devices associated with the oxygen measurement system 70 (FIG. 3).

The computer also includes a transmitter and receiver (not shown) so as to communicate wirelessly with a stationary computer (not shown) which receives the raw signal data from the PUMA system 10 (serial data stream of temperature in volts, pressure in volts, flow in volts, heart rate in beats, CO2 in volts and O2 in degrees of phase shift) and applies the relevant calibrations to each signal to get actual temperature, pressure, flow, and oxygen and carbon dioxide partial pressures. Software in the stationary computer then calculates such relevant metabolic data as ventilatory equivalent, volumetric consumption of oxygen, volumetric production of carbon dioxide, and heart rate, while all of other metabolic quantities can be derived from these measurements. The software for the stationary external computer is essentially a set of routines that are based on a commercially-available software package from Wavemetrics, Inc. (IGOR Pro, http://www.wavemetrics.com).

Operation of PUMA

The results of tests on a human subject are shown in FIG. 4, wherein the volumetric flowrate (V, in liters/minute), and partial pressures of oxygen ($PO_{O2}$) and carbon dioxide ($PP_{CO2}$) are shown as functions of time. The times representing the beginning of an inhalation ($t_{bi}$), beginning of an exhalation ($t_{be}$) and end of an exhalation ($t_{ee}$) are indicated.

Whereas other systems for measuring human metabolism and metabolic rates use gas-analysis and other sensors that are remote from the test subject, and are often not portable, the PUMA system according to the present invention makes all measurements simultaneously and close to the mouth at 10 Hz.

FIG. 4 is a display of data taken by means of the PUMA system from an actual human test subject. PUMA measures the ventilatory equivalent ($V_e$, Eq. I below), production rate of carbon dioxide ($V_{CO2}$, Eq. 2) and consumption rate of oxygen ($V_{O2}$, Eq. 3) by numerically integrating the data in FIG. 4 over an inhale/exhale cycle.

$$\dot{V}_{CO_2} = \frac{\int_{t_{be}}^{t_{ee}} \dot{V}(t) dt}{(t_{ee} - t_{bi})} \quad (1)$$

$$\dot{V}_{CO_2} = \frac{\left[\int_{t_{be}}^{t_{ee}} \dot{V}(t) X_{CO_2} dt\right] - \left[\int_{t_{bi}}^{t_{ee}} \dot{V}(t) X_{CO_2} dt\right]}{(t_{ee} - t_{bi})} \quad (2)$$

$$\dot{V}_{O_2} = \frac{\left[\int_{t_{bi}}^{t_{be}} \dot{V}(t) X_{O_2} dt\right] - \left[\int_{t_{be}}^{t_{ee}} \dot{V}(t) X_{O_2} dt\right]}{(t_{ee} - t_{bi})} \quad (3)$$

where $X_i$ is the mole fraction of species i and is equal to the partial pressure of species i divided by the total pressure.

Note that inhaled $X_{CO2}$ is normally 0.0 and the inhaled $X_{O2}$ is normally 0.21.

The primary innovation PUMA offers, compared to prior art portable devices, is that all gas measurements are made close to the mouth and at a sample rate much greater than other units. All commercial metabolic carts and fixed units measure gas concentrations remotely from the mouth, which allows measurement errors to accumulate. More specifically, the gas from the inhale/exhale streams is sampled and measured at distances ranging from 3 to 10 ft (and beyond), which introduces the potential for gas dilution, and for the introduction of timing and sampling issues that have to be addressed in the analysis of the data. Further, all commercial carts and fixed units make one measurement of oxygen and carbon dioxide, and they assume that concentration is representative of entire single breaths, which misrepresents the potential that is achieved with the present invention, wherein the close-to-the-mouth feature minimizes or eliminates the timing issues present in other portable and fixed commercial units.

Thus, the present invention provides highly time-resolved measurements of human metabolic activity. The present invention further makes use of unique hardware and software for the measurement of oxygen partial pressure.

Although the invention has been illustrated and described in detail in the drawings and foregoing description, the same is to be considered as illustrative and not restrictive in character—it being understood that only preferred embodiments have been shown and described, and that all changes and modifications that come within the spirit of the invention are desired to be protected. Undoubtedly, many other "variations" on the "themes" set forth hereinabove will occur to one having ordinary skill in the art to which the present invention most nearly pertains, and such variations are intended to be within the scope of the invention, as disclosed herein.

The invention claimed is:

1. An apparatus, comprising:
    a manifold configured to be in fluid communication with a mouth of a test subject so as to receive a gas contained in breaths of the test subject;
    a conduit extending from the manifold, wherein the conduit defines a flow channel through which the gas travels; and
    a carbon dioxide sensor attached to the conduit, wherein the carbon dioxide sensor comprises:
        an intermediate support housing enclosing a volume disposed along the flow channel to define a first part of the flow channel;
        an inner support housing attached to a first side of the intermediate support housing, wherein the inner support housing comprises an interior surface which faces the flow channel;
        a plurality of infrared (IR) light emitting diodes (LEDs) mounted on the interior surface;
        an outer support housing attached to a second side of the intermediate support housing, wherein the outer support housing opposes the inner support housing;
        a photodetector attached to the outer support housing, wherein the photodetector faces the flow channel and receives IR radiation emitted by the plurality of LEDs; and
        a narrow bandpass filter disposed between the photodetector and the intermediate support housing, wherein the narrow bandpass filter allows a selected bandwidth of IR energy to reach the photodetector.

2. The apparatus of claim 1, wherein the interior surface is offset from the flow channel such that the plurality of LEDs is separate from the flow channel.

3. The apparatus of claim 2, wherein the interior surface is a concave curved surface.

4. The apparatus of claim 3, wherein the concave curved surface is disposed between upright end walls of the inner support housing, wherein the upright end walls are displaced from edges of the inner support housing such that collars of the inner support housing separate the upright end walls from the edges, wherein the inner support housing is attached to the intermediate support housing via the collars and inner ends of the intermediate support housing.

5. The apparatus of claim 4, wherein the carbon dioxide sensor further comprises a window disposed between the plurality of LEDs and the flow channel, wherein the window is configured to isolate the plurality of LEDs from the gas.

6. The apparatus of claim 5, wherein the window is attached to the upright end walls of the intermediate support housing via gaskets that maintain positioning of the window.

7. The apparatus of claim 6, wherein the window contacts and extends between the inner ends of the intermediate support housing.

8. The apparatus of claim 1, wherein the carbon dioxide sensor comprises pulsing circuitry communicably coupled to the plurality of LEDs, wherein the pulsing circuitry is configured to supply pulse signals to the plurality of LEDs such that the LEDs emit pulsed LED signals into the flow channel.

9. The apparatus of claim 8, wherein the wherein the pulse signals supplied by the pulsing circuitry have a duration of approximately 10 μsecs.

10. The apparatus of claim 9, wherein each of the plurality of LEDs is driven between 1.3 and 2.0 amps at a duty cycle between 0.01 and 0.1 percent.

11. The apparatus of claim 1, wherein the selected bandwidth is between 4.25 and 4.44 microns.

12. The apparatus of claim 11, wherein the plurality of LEDs extends a distance greater than a dimension of the photodetector, wherein each of the plurality of LEDs is aimed to direct its light towards the photodetector.

13. The apparatus of claim 12, wherein the plurality of LEDs comprises:
a central LED; and
a plurality of circumferential LEDS arranged in a circle surrounding the central LED.

14. The apparatus of claim 1, wherein the photodetector is disposed on a thermoelectric cooling device thermally coupled to a heat dissipating fin assembly.

15. An apparatus, comprising:
a manifold configured to be in fluid communication with a mouth of a test subject so as to receive a gas contained in breaths of the test subject;
a conduit extending from the manifold, wherein the conduit defines a flow channel through which the gas travels;
a carbon dioxide sensor attached to the conduit, wherein the carbon dioxide sensor comprises:
an intermediate support housing enclosing a volume disposed along the flow channel to define a first part of the flow channel;
an inner support housing attached to a first side of the intermediate support housing, wherein the inner support housing comprises an interior surface which faces the flow channel;
a plurality of infrared (IR) light emitting diodes (LEDs) mounted on the interior surface;
an outer support housing attached to a second side of the intermediate support housing, wherein the outer support housing opposes the inner support housing;
a photodetector attached to the outer support housing, wherein the photodetector faces the flow channel and receives IR radiation emitted by the plurality of LEDs; and
an oxygen sensor attached to the conduit, wherein the oxygen sensor comprises:
a second intermediate support housing attached to the conduit, wherein the second intermediate support housing encloses a volume disposed along the flow channel to define a second part of the flow channel;
a first housing disposed on a first side of the conduit containing blue light emanating from an optical source, wherein the first housing is configured to direct the blue light into the flow channel;
a second housing disposed on a second side of the conduit, the second housing supporting a sensing disk disposed within the flow channel, wherein the sensing disk has a dye disposed thereon that is excited via the blue light to emit detection light having a differing frequency than the blue light, wherein the excitation of the dye is sensitive to oxygen content of the gas; and
an additional photodetector configured to measure an intensity and a phase shift of the detection light.

16. The apparatus of claim 15, wherein the oxygen sensor is disposed closer to the mouth of the test subject than the carbon dioxide sensor, wherein the first and second housings are directly attached to the conduit and the second intermediate support housing of the oxygen sensor is attached to the conduit via the first and second housings.

17. The apparatus of claim 15, wherein oxygen sensor further comprises:
an optics system disposed within the first housing, the optics system comprising collimating optics configured to:
collimate the blue light prior to the blue light entering the flow channel; and
direct the detection light to the additional photodetector.

18. The apparatus of claim 17, wherein oxygen sensor further comprises;
a component box that is separate from the conduit, wherein optical source is disposed in the component box; and
an optical fiber connecting the component box to the first housing, wherein the optical fiber is configured to direct the blue light from the optical source to the optics system.

19. The apparatus of claim 15, wherein oxygen sensor further comprises a temperature sensor disposed within the second housing, the temperature sensor disposed within the flow channel to measure the temperature of the gas.

* * * * *